(12) United States Patent
Ben-Dor et al.

(10) Patent No.: US 9,995,678 B2
(45) Date of Patent: Jun. 12, 2018

(54) QUANTITATIVE ASSESSMENT OF SOIL CONTAMINANTS, PARTICULARLY HYDROCARBONS, USING REFLECTANCE SPECTROSCOPY

(71) Applicant: Ramot at Tel-Aviv University Ltd., Tel-Aviv (IL)

(72) Inventors: Eyal Ben-Dor, Rishon-LeZion (IL); Gil Eshel, Binyamina (IL); Guy Schwartz, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days. days.

(21) Appl. No.: 15/424,855

(22) Filed: Feb. 5, 2017

(65) Prior Publication Data

US 2017/0146452 A1     May 25, 2017

Related U.S. Application Data

(63) Continuation of application No. 13/916,766, filed on Jun. 13, 2013.

(60) Provisional application No. 61/659,494, filed on Jun. 14, 2012.

(51) Int. Cl.
  *G01N 21/359* (2014.01)
  *G01N 21/3563* (2014.01)
  *G01N 33/24* (2006.01)

(52) U.S. Cl.
  CPC ....... *G01N 21/359* (2013.01); *G01N 21/3563* (2013.01); *G01N 33/24* (2013.01)

(58) Field of Classification Search
  CPC .................................................. G01N 21/359
  See application file for complete search history.

(56) References Cited

U.S. PATENT DOCUMENTS 7,501,285 B1 *  3/2009  Triche ................... G01N 21/64
                                                       422/82.05
2014/0012504 A1   1/2014  Ben-Dor et al.

OTHER PUBLICATIONS

Official Action dated Nov. 10, 2016 From the US Patent and Trademark Office Re. U.S. Appl. No. 13/916,766. (8 pages).
Official Action dated May 19, 2016 From the US Patent and Trademark Office Re. U.S. Appl. No. 13/916,766.

\* cited by examiner

*Primary Examiner* — Manuel A Rivera Vargas

(57) ABSTRACT

Apparatus and method for efficiently assessing the results of reflectance spectroscopy on a soil sample to determine the presence of contaminants in the soil, by constructing a model based on analysis of known samples. The model may be constructed using an all possibilities approach and data mining techniques, on a range of samples, for example of different kinds of soil without pollutants and with different levels of pollutants. The Disclosure relates both to the construction of the model and to its use in the field in analyzing soil contaminants.

13 Claims, 10 Drawing Sheets

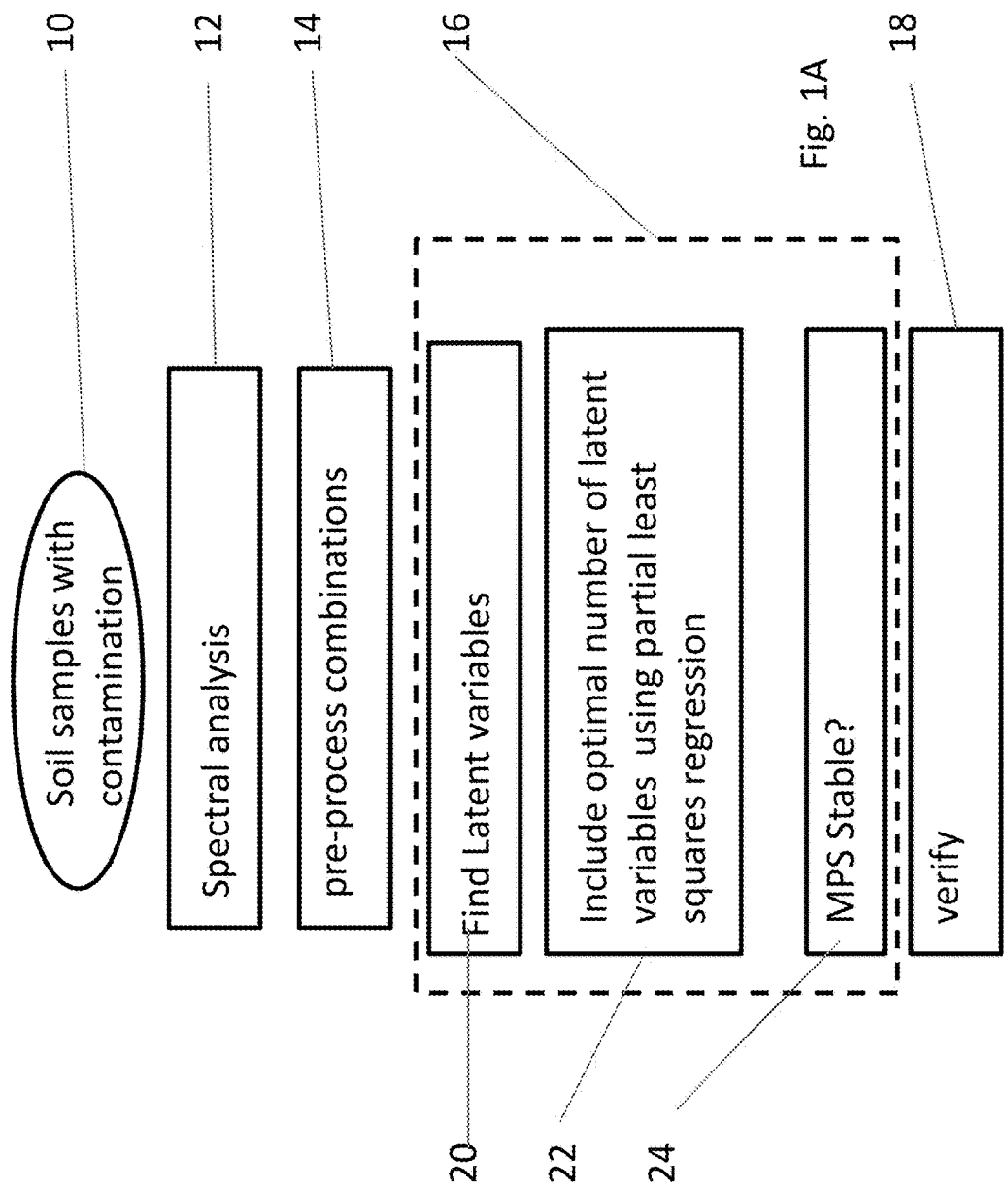

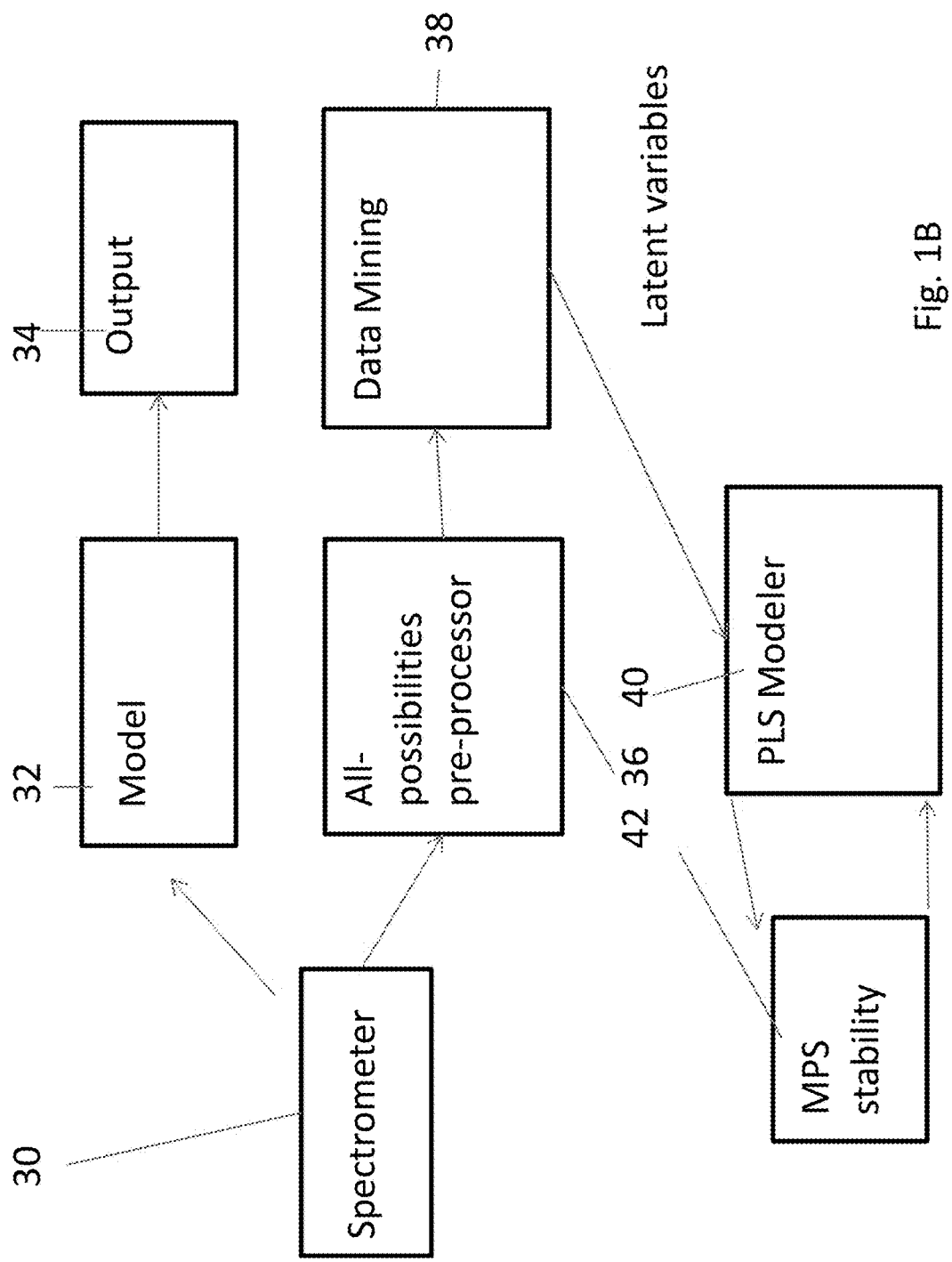

QUANTITATIVE ASSESSMENT OF SOIL CONTAMINANTS, PARTICULARLY HYDROCARBONS, USING REFLECTANCE SPECTROSCOPY

RELATED APPLICATIONS

This application is a continuation of U.S. patent application Ser. No. 13/916,766, filed on Jun. 13, 2013, which claims the benefit of priority U.S. Provisional Patent Application No. 61/659,494 filed on Jun. 14, 2012. The contents of the above applications are all incorporated by reference as if fully set forth herein in their entirety.

FIELD AND BACKGROUND OF THE INVENTION

The present invention, in some embodiments thereof, relates to quantitative assessment of hydrocarbon contamination in soil using reflectance spectroscopy and more particularly but not exclusively to the quantitative assessment of hydrocarbon contamination using near infra-red spectral assessment and a modeling approach such as artificial neural networks, fuzzy logic, partial least squares, support vector machine, and metric learning.

The term "hydrocarbon contamination" is intended to include all kinds of artificial organic pollutants in soil that can be identified by reflectance spectroscopy.

Petroleum hydrocarbons are contaminants of great significance. The commonly used analytic method for assessing Total Petroleum Hydrocarbons (TPH) in soil samples, is based on extraction with 1,1,2-Trichlorotrifluoroethane (Freon 113), a substance prohibited for use by the EPA.

During the past twenty years, a new quantitative methodology has been widely developed that utilizes the reflected radiation of solids. By using this approach, the reflectance radiation across the VNIR-SWIR region (400-2500 nm) is modeled against constituents determined by traditional analytic chemistry methods and then used to predict unknown samples. This technology is environmental friendly and permits rapid and cost-effective measurements of large number of samples. Thus, this method dramatically reduces chemical analytical costs and secondary pollution, enabling a new dimension of environmental monitoring.

With production rates of 13.42 million cubic meters of crude oil per day (Energy Information Administration, 2009), petroleum hydrocarbons (PHC) potential as soil and water contaminants is apparent and of particular significance. PHC are well known to be neurotoxic to humans and animals. PHC were found to affect brain activity and development as well as to cause nausea, disorientation, mental confusion, speech slurring and memory disorders. Exposure to higher levels can cause extreme debilitation, loss of balance, and may even lead to coma, seizures and lethality. Long term exposure is proven to cause changes in neurophysiological or psychological capacity and is further known to induce increased risk of lung, skin and bladder cancer alongside other carcinogenic effects (Hutcheson et al., 1996; Boffetta et al., 1997; Ritchie et al., 2001). For both the diagnosis of suspected areas and the possibility of controlling the rehabilitation process, there is a need to develop and implement a method to rapidly detect and assess PHC in soils.

Due to the complex nature and structure of PHC ingredients, a general measurement index "Total PHC" (TPH) was defined and is the common measurement index for quantifying environmental contamination originated by PHC. The TPH level is determined by the ratio of IR absorption measured per sample extraction, relative to the IR absorption of the EPA standard consisting of 31.5% isooctane, 35% hexadecane and 33.5% chlorobenzene.

The common method for assessing TPH in soil samples is based on the no longer approved Environment Protection Agency (EPA) method 418.1. The EPA withdrew this method due to the use of Freon 113, an ozone depleting material. Nevertheless, this method is still commonly used worldwide, in some countries (i.e. Israel), this method is the only method used for site investigation. The method was developed originally to assess TPH in waste water but was later adjusted in order to assess TPH in soil samples. Not only was this method withdrawn by the EPA, but it is also problematic for various other reasons such as the need for skilled operators, the process length and cost, the difficulties in using it in situ, availability of the extracting solvent being very limited, the need for transporting samples to the laboratory etc.

The spectral properties of hydrocarbons were identified in the late 1980's, although it was argued that these properties are only visible at concentrations of 4% wt. and above (Cloutis, 1989). In the mid 1990's a NIR reflectance sensor was developed as a proof of concept for the detection of organic matter in soil, based on the spectral properties identified by Cloutis (ibid). The sensor was designed for the detection of Benzene in soil at a minimal concentration of 4.4% wt, several configurations were tested and minimal information is provided (Schneider et al., 1995). Soon after, the U.S. Department of Energy contracted a private company to investigate the application of reflectance spectroscopy as a tool to determine motor oil contamination in sandy loam. A schematic design for a field instrument was suggested, but only one type of PHC contaminant and one type of soil were tested. In addition, a small number of samples were used at a very limited contamination range (Stallard et al., 1996).

A more inclusive study was conducted shortly after using three types of soil contaminated in the laboratory with diesel and gasoline. 0.1% wt. and 0.5% wt. minimum detection limits were achieved respectively (Zwanziger and Heidrun, 1998). The first study utilizing field collected samples, was not able to produce robust models but rather led to very low correlations (r=0.68) and large errors, probably due to the limited number of samples and problems with the analytic chemistry measurements done by the laboratory that produced inconsistent measurements (Malley et al., 1999). Attempts at mapping hydrocarbons using the Landsat and Daedalus sensors in 1994 and 1995 failed, probably due to the limited spectral resolution of the sensors (multispectral sensors, 7 and 12 bands respectively) (Kühn and Hörig, 1995; Hörig et al., 2001). Nevertheless, a later study, utilizing the higher spatial and spectral resolutions as well as the very high signal to noise ratio of the HyMap HSR airborne scanner (128 bands) (Cocks et al., 1998), yielded a successful identification of hydrocarbons and oil contaminated soils but for high consecrations only (2.5% wt) (Hörig et al., 2001). Based on the HyMap mission, a Hydrocarbon Index was developed for mapping hydrocarbon bearing materials. This index is limited to very high signal to noise ratio sensors as well as other issues, such as problems with land cover, vegetation and high concentration detection levels (Kühn et al., 2004).

The most comprehensive work on reflectance properties of hydrocarbons was conducted by Winkelmann (2005): several types of hydrocarbons were mixed with several types of soil under laboratory conditions. They were measured spectrally and an attempt was made to separate them into hydrocarbon groups using the reflectance spectra; hyperspectral airborne remote sensing was also applied to identifying hydrocarbon contamination. No quantitative models were tested, although this was mentioned as an avenue of further study (Winkelmann, 2005). A recent study by Chakraborty et al. (2010) on the prediction accuracy of VNIR-SWIR reflectance spectroscopy of petroleum contaminated soil, showed fair validation results ($R^2$=0.64). The study included 46 field collected samples that were preprocessed and modeled by several techniques.

Chakraborty et al. continued collecting field samples, and applied the statistical approach of the previous study. By using kriging, they produced TPH distribution maps of the contaminated site that match well with the topography of the study site. Sorak et al. started exploring the possibility of using a hand held Phazir portable spectrometer for TPH determination. They started by preparing several artificially contaminated samples in the laboratory with diesel and oil and creating Near Infrared Analysis (NIRA) models.

While the above mentioned studies addressed concentration levels of 0.1% wt and above, nowadays environmental regulations require precision levels of an order of magnitude lower. A comprehensive research including several types of PHC at a wide concentration range is needed, especially at very low concentrations.

During the past twenty years, a new quantitative methodology named NIRA (Near Infrared Analysis) or NIRS (Near Infrared Spectroscopy) has been widely developed (Williams and Norris, 1987). This approach was adopted 40 years ago from a strategy developed in the food science discipline (Ben-Gera and Norris, 1968a; b), whereas today it is widely utilized in many industrial and scientific applications. By using the NIRA approach the reflected radiation across the VIS-NIR-SWIR region (400-2500 nm) is modeled against constituents determined by traditional chemical analysis. The constructed model is then used to assess unknown samples. Visible light has also been used.

In order to remove any irrelevant information, which cannot be handled properly by the modeling techniques, spectral preprocessing techniques are used. The preprocessing techniques include averaging, centering, smoothing, standardization, normalization and transformations, among others.

Introduced in 1983 by Wold et al., partial least squares regression (PLS) is similar to principal component regression (PCR), but in PLS the principle components or latent variables (PCs, LVs) are constructed such that they include the chemical reference (Y variables, dependent data) in the calculation process. This technique orders the PCs according to their relevance for predicting the dependent variables, rather than to their description of the most variance of the spectral data. This method excels when the dependent data (X variables) express common information, as usually happens in spectral data. The required number of PCs is typically smaller than that in a PCR calibration model for similar model performance (Wold et al. 1983; Esbensen et al. 2002; Nicolaï et al. 2007). As the PLS process is based on LVs, using the optimal number of LVs (nLV) is crucial. On one hand including as much data as possible will improve performance, but on the other hand only the first LVs represent the relevant data whereas the rest are noise (Esbensen et al. 1994). Keeping the model as simple as possible by using the minimum number of LVs is very important to prevent over fitting, but it is also critical to include all the LVs that contain the data relevant for the modeling process in question. In short, the optimal nLV should be selected for representing the property in question and not the noise.

Modeling of spectroscopy data refers to relating a set of spectral parameters that are derived from the spectral information (before or after the aforementioned preprocessing treatment), to the chemical or physical properties of the material in question by using a set of well-known samples. The data are divided into three groups: training, validation and test. The relationship between the property in question and the spectroscopy data is found via the training group and simultaneously cross-validated by the validation group. Finally, the model is applied to the test group, independently of the training and validation processes. Division of the data into the training, validation and test groups is done by using a well known algorithm (Minasny and McBratney, 2006) that takes into account the reference values distribution in order to create the training, validation and test groups in a way that would best represent the entire dataset.

Reflectance spectroscopy permits environmental friendly, rapid and cost-effective measurements of many samples and therefore functions as a substitute for the costly and time consuming chemical analysis. Due to the numerous combinations of preprocessing techniques as well as dataset divisions there is a lack of effective tools to allow reflectance spectroscopy methods to be used effectively in situ and so today it is not possible to provide an automated and optimized NIRA modeling system for hydrocarbon contamination analysis in soils in a way which is rapid, accurate, and cost effective, solely from reflectance spectroscopy.

SUMMARY OF THE INVENTION

The present embodiments provide a method for efficiently assessing the results of reflectance spectroscopy on a soil sample to determine the presence of contaminants in the soil, by constructing a model based on analysis of known samples. The model may be constructed using an all possibilities approach and data mining techniques, on a range of samples, for example of different kinds of soil without pollutants and with different levels of pollutants. The present disclosure relates both to the construction of the model and to its use in the field in analyzing soil contaminants.

An embodiment is a way of efficiently assessing the results of reflectance spectroscopy on a soil sample to determine the presence of contaminants in the soil, by constructing a model based on analysis of known samples. An exemplary model is the partial least squares regression model referred to above, however, the model is constructed using an all possibilities pre-processing approach and data mining techniques as will be discussed hereinbelow, on samples of different kinds of soil without pollutants and with different levels of pollutants. It was noted by the present inventors that NIRA calibration processes can be strongly affected by the various preprocessing techniques, and thus a new "brute force" approach is suggested; in which all possibilities of common preprocessing methods are tested before the modeling stage is applied.

According to an aspect of some embodiments of the present invention there is provided a method and apparatus for quantitative assessment of hydrocarbon contamination in soil using reflectance spectroscopy and a model. The near infra-red spectral region may be used with partial least squares assessment, and an all-possibilities approach may be used, as will be explained below.

According to a further aspect of the present invention there is provided a method and apparatus for construction of a stable model for reflectance spectroscopy assessment of soil for contamination assessment.

The model may be generated using an all possibilities approach on a range of test samples of different kinds of soils with different contaminations. The samples are analyzed using spectroscopy or spectral imaging, and the spectral datasets may be preprocessed in different ways, as detailed herein. In the all-possibilities approach, a set of multiple different preprocessing techniques are provided which operate on the spectral data, and different combinations of the preprocessing operations are carried out on the data. In theory all possible combinations of the techniques may be used, and thus for a set of eight preprocessing operations, 250 data sets may be created. However in practice certain combinations make no sense, so typically only 120 of the 250 possible datasets would be used. Furthermore, different numbers and types of samples may be used.

The modeling may lead to multiple initial model results, which can then be selected for stability.

The performance of the model may be assessed using a model performance scoring (MPS) parameter, which may be defined as MPS=% Stability+NRPD−NRMSEP−NnLV.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. The data processor may include a volatile memory for storing instructions and/or data and/or a non-volatile storage, for example, a magnetic hard-disk, flash memory and/or removable media, for storing instructions and/or data. A network connection may be provided and a display and/or a user input device such as a keyboard or mouse may be available as necessary.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A is a flow chart showing a process for generating a model for analyzing soil samples according to a first embodiment of the present invention;

FIG. 1B is a block diagram of a device for generating the model of FIG. 1A and also for using the model to test soil samples;

DESCRIPTION OF SPECIFIC EMBODIMENTS OF THE INVENTION

Figure 2A:
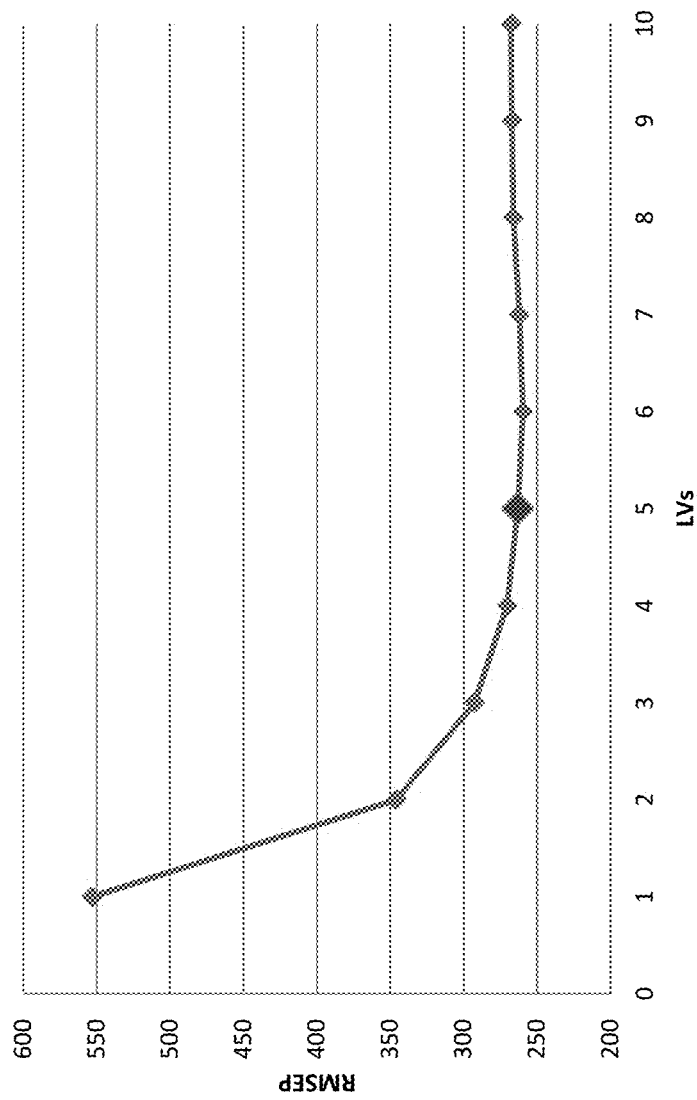
FIG. 2A is a graph showing an example of a stable model.

The present invention, in some embodiments thereof, relates to quantitative assessment of hydrocarbon contamination in soil using reflectance spectroscopy.

The present embodiments adapt the quantitative methodology referred to above, by use of the above-mentioned all-possibilities approach, and develop steps in which hydrocarbon contamination in soils can be determined rapidly, accurately, and cost effectively solely from reflectance spectroscopy. Artificial contaminated samples are analyzed chemically and spectrally to form a database of 5 soils contaminated with 3 types of PHC, creating 15 datasets of 48 samples each at contamination levels of 50-5000 wt % ppm. A brute force preprocessing approach combines 8 different preprocessing techniques at all possibilities, resulting in 120 different mutations for each dataset. A computing system that supports the all-possibilities approach was developed for this study and is discussed below. A new parameter for evaluating model performance scoring (MPS) is provided based on a combination of several common statistical parameters. The data is divided into training, validation and test sets and resulting effects on modeling accuracy are shown. The results predict TPH levels at low concentrations in selected soils at relatively high precision levels. Dividing a dataset into training, validation and test groups affects the modeling process and different preprocessing methods or their combinations need to be selected based on soil type and PHC type. MPS was found to be a better parameter for selecting the best performing model than RPD, yielding models with the same performance but which were less complicated and more stable. The use of the all possibilities system proved to be useful for efficient optimal modeling of reflectance spectroscopy data.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to FIG. 1A, a method for quantitative assessment of hydrocarbon contamination in soil using reflectance spectroscopy is shown in a flow chart.

An initial stage 10 involves obtaining soil samples from several different soil types having different hydrocarbon contamination levels.

Each sample is analyzed using spectral imaging or spectroscopy, to obtain spectroscopy data of the sample in stage 12.

In stage 14 different combinations of preprocessing operations are applied to the spectroscopy data obtained in the previous stage. A set of preprocessing operations is provided and all possible combinations are set up. Then certain combinations which make no sense or introduce excessive complications may be removed, and each remaining combination is used to generate a separate mutation of the data set.

Then in box 16, a model is built up using all of the mutations. The model relates the preprocessed spectral data to the different soils and contamination levels.

The model may then be verified in box 18 using the model with spectroscopy data of soil samples of known contamination, and finally the model is used against unknown samples to determine the unknown contamination.

The model in box 14 may be any data mining model. In an embodiment the model was built using data mining processes to indicate latent variables—box 20. The latent variables are added one by one in an iterative process to the model, using partial least squares regression, and retained if they reduced the estimation error, until an optimal number of latent variables were included—box 22.

Aside from latent variables, any other method of dimension reduction or wavelength selection may be used in a suitable modeling technique.

The model is tested for stability in box 24, as will be described later.

In an embodiment, the set of preprocessing operations includes initial smoothing, multiplicative scatter correction, standard normal variate, absorptance, continuum removal, first derivative, second derivative, and final smoothing. The all possibilities approach involves generating all the reasonable combinations of the above set.

Typically the reasonable combinations are between a third and a half of all possible combinations, so that for the above eight operations, the total possibilities are 256 combinations, but only 120 of these are considered reasonable.

For example, from all the possible combinations one may exclude for example those combinations that contain mutually incompatible preprocessing operations, and combinations that provide results that are complex numbers containing imaginary components.

In the above, model stability was mentioned. The model may be tested using a model performance scoring parameter (MPS) defined as:

MPS=% Stability+NRPD−NRMSEP−NnLV wherein the % Stability is obtained by dividing a number of stable models by a number of repetitions for each mutation, NRPD is a normalized average of a ratio of prediction to deviation, NRMSEP is a normalized root mean square error in prediction, and NnLV is a normalized optimal number of latent variables.

The spectroscopy used may be near infra-red spectroscopy, in which case the spectral imaging or spectroscopy may be carried out within a wavelength range lying between 350 and 2500 nm.

Data mining operations that may be used may comprise both linear and non-linear algorithms.

The data mining operations may include artificial neural networks, genetic algorithms, support vector machines, fuzzy logic, partial least squares, multiple linear regression and principle component regression.

The pre-processed spectroscopy data may be arranged into datasets using conditioned Latin Hypercube Sampling. Data may be needed for separate training, validation and test sets and the way the data is divided may affect the final model.

Reference is now made to FIG. 1B, which shows a testing device that can be used both for building the above-described model and then, once a model is available, for testing soil samples for contamination.

The testing device includes a spectrometer 30, and a model 32, which is constructed as described above. The model relates a set of spectral parameters obtained from spectroscopy data to the chemical contamination properties. The spectral parameters are obtained from the spectroscopy data as discussed following mutation using combinations of the spectral preprocessing operations, as explained. An output 34 indicates the contamination state of the sample as predicted by the model from spectral parameters obtained by the spectrometer.

In order to construct the model, the device has an all-possibilities preprocessor 36, which preprocesses the spectral data using all the relevant combinations of preprocessing operations to form different mutations of the data. A data mining unit 38 then looks for latent variables in the data and a PLS modeler 40 adds latent variables one by one to the model provided that the variables being added increase the stability of the model. The stability of the model is tested by MPS stability unit 42.

Materials and Methods

Soils and Hydrocarbons

Five soils were selected for the present study. The soils taken were defined according to the local definition system (Dan and Koyumdjisky, 1963) as well as the USDA key (Staff, 2010) as being Loess (Tipic Xerofluvent), Hamra (Tipic Xerocherept), Gromosol (Typic Chromoxerert), Rendenzina (Lithic Haploxeroll) and Terra Rosa (Lithic ruptic Xerochrept). These soils represent a wide range of soil properties as described in Table 1. The soils were collected from areas that were assumed to have no PHC contamination and were air dried and sieved through a 2 mm sieve twice. The soils properties were determined using common methods as follows: Hydroscopic moisture content was determined by weight loss after 24 h at 105° C. pH level and electrical conductivity were determined with a laboratory bench top 86505 pH/Conductivity meter by M.R.C Ltd. in 1:2 soil and deionized water (respectively) after reaching equilibrium (30 minutes). Specific surface area (SSA) was determined by the absorption of a mono layer of ethylene glycol monoethyl ether (EGME) (Carter et al., 1986). Particle size distributions were determined by Malvern Mastersizer 2000 following Eshel methodology (Eshel et al., 2004). SOC, SIC and Total N were determined by a flash CHN elemental analyzer (Thermo Scientific Flash 2000).

Then, laboratory contaminated samples were prepared by mixing known weights of several PHC types including: Octane Fuel, Diesel and Kerosene with known quantities of soil. For making well mixed low concentration samples, we initially mixed a batch of 99.5 gr of soil with 0.5 gr of the selected PHC; the batch was then mixed again with clean soil at 48 concentration levels. In order to minimize the loss of PHC components, we minimized exposure to open air as much as possible. Each sample was placed in an amber glass vial, capped with a PTFE lined cap at and kept at 4° C.

Spectroscopy Measurements

All samples were measured spectrally using an ASD Field spec PRO spectrometer (ASD Inc., Boulder, Colo.), each measurement included 2150 wavelengths between 350 and 2500 nm at 1 nm intervals. A Spectralon (Labsphere, NH, USA.) surface was used for the calibration of the spectrometer and as a relative target. Each sample was measured 3 times using a self-illuminated contact probe (ASD Inc., Boulder, Colo.). An average spectrum was calculated as the representative spectrum for each sample, as the standard deviation was negligible. The first 100 (350-450 nm) and last 50 (2450-2500 nm) bands were removed due to noisy signal; the remaining 2000 bands (450-2450 nm) were used as the X-Data for the chemometric analysis.

Wet Chemistry—TPH Chemical Analysis

For each set of laboratory prepared samples, several samples were tested for validating the mixture concentration. A method for TPH measurements in soil was used that is based on the adjusted EPA 418.1 method that was originally designed for waste water. The process included extracting the hydrocarbons from 3 gr of soil sample in 15 ml of 1,1,2-TrichloroTrifluoroethane (Freon 113, PESTI-S) and adding 2 gr of sodium sulfate (Anhydrous, AR) for absorbing water and increasing the ionic strength of the solution. The mixture was then placed in an ultrasonic bath for hasting the process of separating the hydrocarbons from the soil matrix. The extracted solvent was then mixed with Silica Gel 60 (0.063-0.200 mm) for the absorption of polar hydrocarbons commonly found in soil organic matter, and placed on a magnetic stirrer for 10 minutes. The mixture was then filtered with an ash-less filter paper (Whatman 44). Finally the mixture of Freon 113 and non polar hydrocarbon (PHC) was then placed in an Infrasil quartz cuvette and the TPH level was determined by a TPH analyzer (Buck scientific Inc. model HC-404) calibrated by standard TPH solutions (Buck scientific Inc. EPA method 418.1 reference standard part #404-11).

Preprocessing the Spectral Data

Each of the 15 data sets was preprocessed using the following preprocessing techniques including all of their possible combinations:

1. Initial Smoothing—Spectral data can be smoothed by running a smoothing algorithm, thus removing noise (while it is important to remove noise, weak signals can be affected as well). I.e. the moving average of a spectrum can be obtained by first taking the average of a fixed small subset size of the spectrum. The fixed subset size is then shifted forward, creating a new subset of numbers, which is averaged. This process is repeated over the entire data series. Smoothing is very important when modeling data especially if the data is noisy or derivatives are involved.
2. Multiplicative Scatter Correction (MSC)—MSC is used to compensate for additive and/or multiplicative effects in spectral data and is one of the most commonly used normalization techniques (Geladi et al., 1985). MSC was originally designed to deal with multiplicative scattering alone. However, a number of similar effects can be successfully treated with MSC, such as: path length problems, offset shifts, interference, etc. The idea behind MSC is that the two effects, amplification (multiplicative) and offset (additive), should be removed from the spectral data to avoid dominating the information (signal) in the spectral data. In MSC the light scattering is estimated for each sample relative to an ideal sample that is obtained by averaging the complete wavelength range of the data set. Each spectrum is then corrected, such that all samples appear to have the same scatter level as the reference spectrum (Geladi et al., 1985).
3. Standard Normal Variate (SNV)—is a row-oriented transformation which centers and scales individual spectra (Barnes et al., 1989). Each value in a row of data is transformed according to the formula:

New value=(Old value−mean(Old row))/Stdev(Old row)

Like MSC, the practical result of SNV is that it removes scatter effects from spectral data. An effect of SNV is that on the vertical scale, each spectrum is centered on zero and varies roughly from −2 to +2. Apart from the different scaling, the result is similar to that of MSC. The practical difference is that SNV standardizes each spectrum using only the data from that spectrum; it does not use the mean spectrum of any set like MSC (Barnes et al., 1989). The choice between SNV and MSC is a matter of personal preference; however it is important to note that when combined with transformation of absorbance, results will include complex numbers with imaginary parts that cannot be modeled in PLS.
4. Absorption—Spectral data performed in transmission mode can be quantified using Beer's Law (concentration-~log(1/T) where T is the transmitted radiation). Accordingly, reflectance measurements are frequently converted to log (1/R) values, which are then used in a manner similar to reflectance readings (Nicolaï et al., 2007).
5. Continuum Removal—The continuum is the background absorption on which other absorption features are superimposed. The spectrum is divided by a convex hull that is fitted over it (Clark and Roush, 1984; Clark and others, 1999).
6. First Derivative—Derivation is often used to remove baseline shifts and superposed peaks. Derivatives are usually calculated according to the Savitzky-Golay algorithm (Savitzky and Golay, 1964). The parameters of the algorithm (interval width, polynomial order) should be carefully selected to avoid amplification of spectral noise (Naes et al., 2002; Nicolaï et al., 2007).
7. Second Derivative—While similar to the first derivative, second derivative spectra can correct for both additive and multiplicative effects (like MSC) (Naes et al., 2002; Nicolaï et al., 2007).
8. Final Smoothing—Running a smoothing algorithm (as described above) after other preprocessing methods can help reduce noises that were amplified especially if derivatives were involved.

Using all possible combinations of the mentioned preprocessing methods potentially yields 256 different mutations of the dataset. In practice, 120 mutations are generally used as some of the combinations are unreasonable, for example using both MSC and SNV, using both first and second derivatives and combining SNV (which results in negative values) with absorbance transformation that would produce results with complex numbers with imaginary parts that cannot be modeled in PLS.

Additional pre-processing options for spectral data are known in the literature, and further options may be added as additional members or may be used to replace existing operations in the dataset. Furthermore, additional options may be developed over the lifetime of the patent and also incorporated into the preprocessing techniques used. It will be appreciated that changing the total number of preprocessing techniques changes the total number of combinations. Exchanging individual preprocessing operations will change the number of reasonable combinations independently of the total number of combinations.

Modeling Process

Before the modeling process, we divide each dataset into three groups: training, validation and test. The relationship between the chemistry and the spectroscopy data may be found via the training group and may be simultaneously cross-validated by the validation group. Finally, the model may be applied to the test group, independently of the training and validation process.

Samples may be divided in the following manner: 75% for training and validation (validation was done by the leave one out method) and 25% for test. In an experiment 36 samples were used for training and validation and 12 samples for testing. For reliable results that represent the entire dataset as best as possible the Conditioned Latin Hypercube Sampling (cLHS) method may be used (Minasny and McBratney, 2006). cLHS is a stratified random procedure that provides an efficient way of sampling variables from their multivariate distributions. 100,000 random divisions were created, and then the distributions of the Y values are examined. The dataset division in which the distributions of the training/validation group and the test group are most similar to the entire dataset is then selected. The data is divided into training/validation and test groups based on the cLHS algorithm that ensures these groups represent the dataset very well. Nevertheless, each time we divide a dataset into these groups, slightly different groups are created, affecting the modeling process to some extent.

In the experiment, the above procedure was repeated 10 times for each dataset, thus, in fact, creating 1200 PLS models for each dataset consisting of 120 mutations at 10 different modeling scenarios based on the training/validation and test groups selections. The results of the 1200 PLS models were then consolidated to statistically quantify the effects of the preprocessing method, as well as the training/validation and test group selection process on the modeling results. During the consolidation process, several statistical parameters were calculated: Average number of latent variables (nLV avg), number of latent variables standard deviation (nLV std), average test group $R^2$ (Test $R^2$ avg), test group $R^2$ standard deviation (Test $R^2$ std), average RMSEP (RMSEP avg), RMSEP standard deviation (RMSEP std), average RPD (RPD avg), RPD standard deviation (RPD std) and % Stability.

The best models for each dataset based on the highest average RPD value of the 10 repetitions of each mutation are shown in table 2.

PLS

The first stage of the modeling process includes a selection process for the optimal number of LVs to use (nLV). The selection of the nLV procedure is based on an iterative process, in which a model is built using the first LV only and the root mean square error of prediction (RMSEP) is recorded, then the next LV is added and the RMSEP is recorded once again and so on. This process is repeated for the first ten LVs. As we add LVs the RMSEP decreases, indicating a better model, unless, the added LV contains mostly noise and then the RMSEP increases (Esbensen et al., 2002). The optimal nLV may be determined by selecting the nLV that produces the lowest RMSEP, then backtrack and include a LV only if it improves the RMSEP by at least 2%. After the optimal number of the LVs to use has been determined, PLS may be used to construct a model for predicting the wt % ppm for each dataset (Soil type+PHC type) based on the spectral data, for each of the 120 mutation of that data set. The model may then be used to predict the test group and the following statistical parameter may be calculated: $R^2$, RMSEP, and Ratio of Prediction to Deviation (RPD). The best mutation for that dataset may then be determined by the highest RPD value, results are shown in Table 2.

Model Stability

A model is considered stable when all LV used reduce the RMSEP, and unstable otherwise. The % Stability may be calculated by dividing the number of stable models by the total number of repetitions for each mutation.

Model Performance Scoring (MPS)

While RPD value is a well known statistical modeling criteria to evaluate performance of NIRS models (Williams and Norris, 1987), we propose that additional statistical factors should be considered in order to achieve stable and constant models. The MPS system suggested herein for better evaluating NIRS model performance, is based on a combination of several statistical parameters: % Stability, RPD avg, RMSEP avg and nLV avg. The MPS is based on all 120 mutations of each dataset; each statistical parameter value is normalized between 0 and 100 so the statistical parameters will have the same weight. Based on the position of a statistical parameter of a specific mutation relative to the range of this statistical parameter in the dataset, the statistical parameter is normalized. The highest value will be 100, the lowest value will be 0, and the rest of the values are linearly stretched between. As we use the average result of each statistical parameter we also include the modeling effects of the data division into the training/validation and test groups. The % Stability and normalized RPD avg (NRPD) are added to the score because higher values are better, the normalized RMSEP avg and nLV avg (NRMSEP, NnLV respectively) are subtracted from the score because lower values are better. MPS can range between a theoretical 200 (the best case scenario) and −200 (worst case scenario). A general equation for calculating MPS is shown in Eq 1.

$$\text{MPS}=\%\text{ Stability}+\text{NRPD}-\text{NRMSEP}-\text{NnLV} \qquad [\text{Eq. 1}]$$

Using Eq. 1, we select the best model of each dataset; results are shown in Table 2.

"All Possibilities" Approach: The Paracuda System

Figure 3:
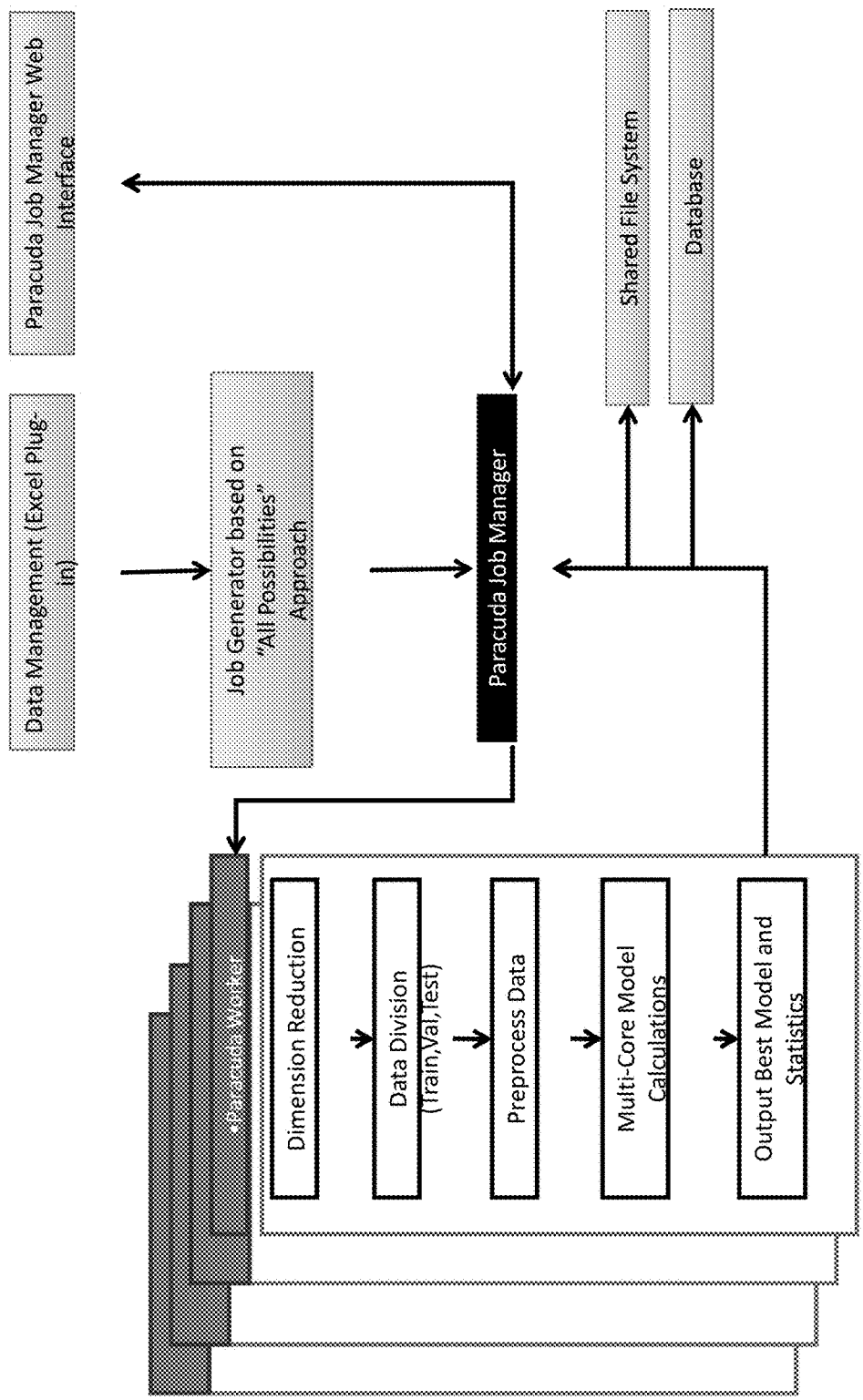
FIG. 3 is a simplified diagram showing an architecture for blocks used in operation of the present embodiments.

Managing and deploying thousands of chemometric models and preprocessing method combinations requires an automated system and distributed computing, whereas manual management and deployment of these tasks is impossible. Reference is now made to FIG. 3, which is a schematic block diagram of a modeling and data mining software system developed by Novospec ltd. and the Remote sensing laboratory at the Tel Aviv University, for exploring very large datasets and finding the hidden patterns and relationships within the data. The system, referred to hereinafter as Paracuda, may handle spectroscopy data and may model spectroscopy measurements against chemical constituents, for creation of robust prediction models. The Paracuda system is based on finding the most important variables (or wavelengths when dealing with spectroscopy data) and thus minimizing the amount of data needed to be analyzed. Paracuda utilizes the parsimony concept for avoiding situations where models that have good calibration results are in fact over-fitted and produce poor results when the test data is presented. Paracuda is suitable for using pretreatment of the data presented using multiple preprocessing methods and their combinations, as described in the materials and methods section. Due to the vast world of data mining algorithms Paracuda employs what is known as an all possibilities approach. The all possibilities approach applies state-of-the art linear and non linear algorithms combined with preprocessing methods for modeling the data, including Artificial Neural Networks (ANN), Genetic Algorithms (GA), Support Vector Machines (SVMs), Fuzzy Logic (FL), Partial Least Squares (PLS), Multiple Linear Regression (MLR), Principle Component Regression (PCR) and others. Such an all possibilities approach, which includes testing multiple preprocessing methods and their combinations, dimension reduction and different modeling techniques, requires heavy processing power, and therefore Paracuda may be operated on a grid based supercomputer with multiple processing cores for rapid analysis. The system is easy to operate via an excel plug-in and a web interface that enables easy and fast data transfers to the Paracuda servers, changing modeling parameters for advanced users (a full automatic mode is the default) as well as controlling current jobs and monitoring their progress. The output produced by Paracuda includes job information, preprocessing and dimension reduction information, if applicable, of the best models developed and their statistics. The server side architecture of the Paracuda system consists of multiple components: Job Manager, Job Generator, Shared file system, Workers and various other modules, for Dimension Reduction, Data Division, Preprocessing, Excel Generator etc. In the presently described experiment, the Paracuda software suite was used to preprocess, divide the data and employ the PLS modeling method for all 15 datasets. The results of this study are the consolidation of the 18,000 PLS models output of the Paracuda system.

Results And Discussion nLV Selection

Figure 2B:
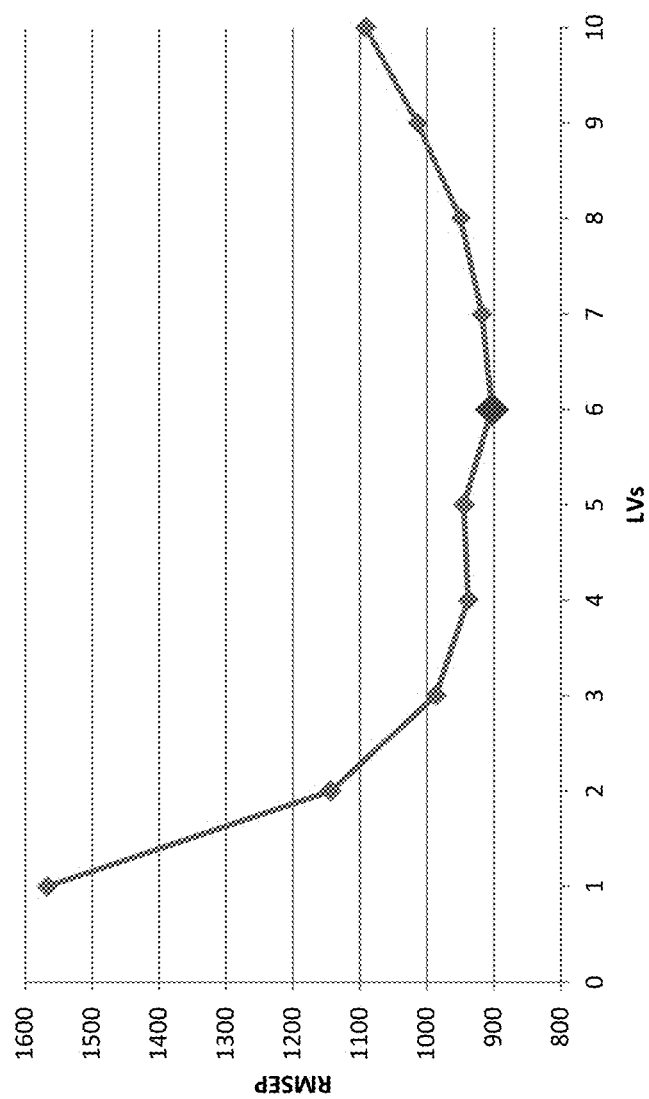
FIG. 2B is a graph showing an unstable model.

A sample plot of the RMSEP change when adding LVs for Loess soil contaminated with diesel dataset that underwent smoothing and first derivative preprocessing is shown in FIG. 2A. From FIG. 2A it is clear that only the first 6 LVs contain information that benefits the modeling process; nevertheless, a threshold was set that a LV will be used only if it improves the RMSEP by at least 2%. In the case of FIG. 2A, while using LV number 6 improves the RMSEP a bit, it does not improve by more than 2% and therefore in this case only 5 LVs are selected. In some cases, one of the LVs used in the modeling process increases the RMSEP, but the following LVs contribute only to decrease the RMSEP, directing the use of the LV in the modeling process. FIG. 2B shows an example of an LV to RMSEP plot of an unstable model for Loess soil contaminated with diesel that underwent MSC and second derivative preprocessing. In the case presented in FIG. 2B, it is clear that one should use 6 LVs although LV number 5 does not decreases the RMSEP, but rather increases it.

Modeling Performances and Soil Properties

Figure 7A:
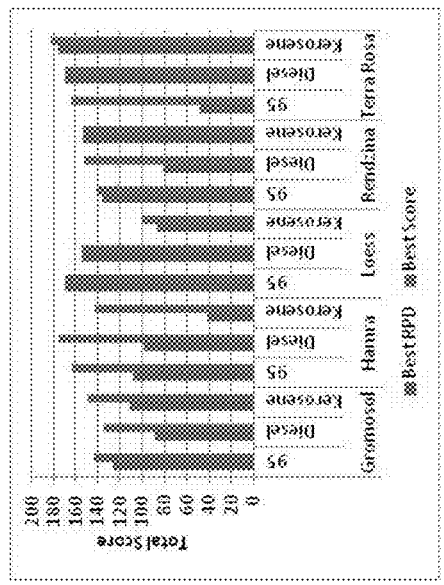
FIGS. 7A-7F are comparisons of best RPD models with best score models.
Figure 7B:
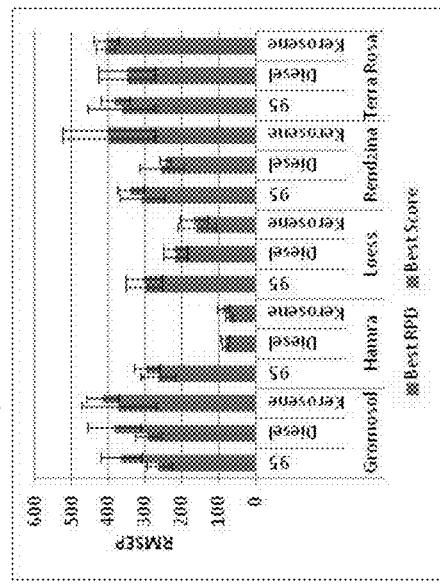
Figure 7C:
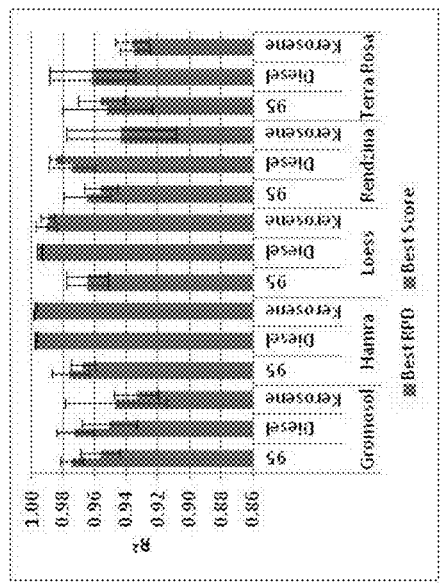
Figure 7D:
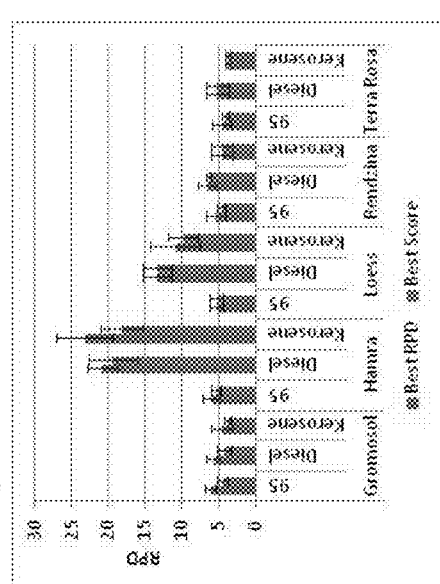
Figure 7E:
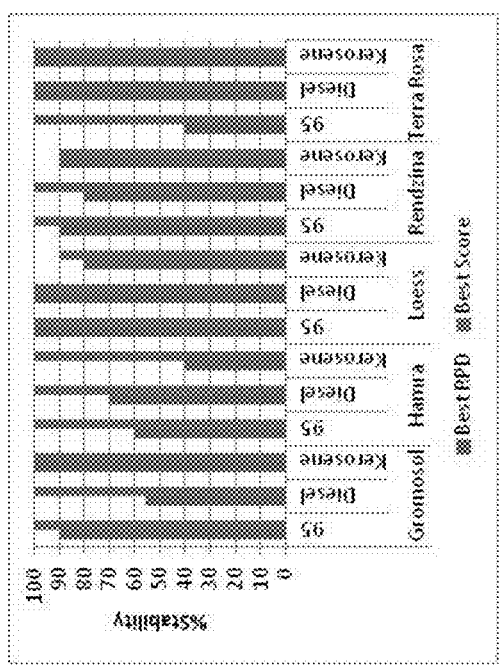
Figure 7F:
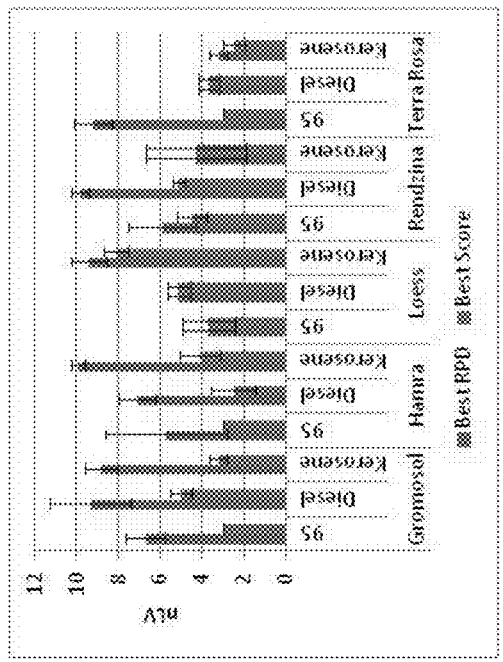

Referring now to FIG. 7C, there are shown Hamra and Loess soils contaminated with diesel and kerosene, which correspond to Datasets 5, 6, 8 and 9 of Table 2. Such datasets are the datasets having the best performing models, with average RPD values of over 20 and 10 respectively. In the present experiment we found that coarse soil particles were indicated by low SSA and reduced albedo levels, and finer soil particles were indicated by higher SSA yields and higher albedo levels. The soil matrix reflectance is equivalent to the background and the contaminant reflectance is the target to be modeled. We hypothesize that when we try to quantify the contaminant in the soil matrix, the relative reflectance contribution of the matrix with high SSA relative to the contribution of the contaminant is much higher, making the modeling more difficult. Therefore, the low SSA of the Hamra and Loess soils can explain the better performing models. As the soil brightness affects the Signal to Noise Ratio by producing a better signal, the brighter soils yields better performing models. Taking into consideration both brightness and SSA, Hamra soil models perform better than Rendzina or Loess soil models although the latter are brighter. Rendzina soil models did not perform as well as Hamra and Loess soils due to its high SSA even though the Rendzina is a very bright soil. The suggestion of the current study is that SSA is a significant factor.

Optimal Model Selection

RPD is commonly used as a parameter for evaluating the performance of chemometric models, as it incorporates both the modeling error and the Y variables value range. A comparison of the best models selected by the highest RPD versus the best models selected by the best MPS (described in the previous section) is shown in FIGS. 7A-7F. From FIG. 7, it is clear that there is no significant difference in RPD, RMSEP or $R^2$ (FIG. 7A, 7B, 7C), although models selected by the best MPS show better stability (FIG. 7E) and use fewer LVs (FIG. 7F) significantly.

While the best MPS model for a specific dataset may yield the same performance as the best RPD model of the same dataset, the best MPS model may be more stable and simpler. In some cases (Datasets 7, 8, 12 and 14) the best MPS model is also the best RPD model, as shown in Table 2.

Table 2 shows that modeling efficiency depends on both soil type and PHC type. In general the brighter the soil and the heavier the PHC, the easier it is to model. The resulting models from these datasets yield the best performances they could reach i.e. an average RPD of ~23 and average RMSEP of ~73 (hamra soil contaminated with kerosene dataset). Nevertheless, dark soils and lighter PHC also yield fair results with an average RPD of ~4 and average RMSEP of ~400. The effect of preprocessing on the modeling outcome is critical and could mean the difference between a non-working model and an excellent model. For example, the dataset showing loess contaminated with diesel contains results ranging from an RPD of 4 to an RPD of 14, or even an RPD of under 1 in some cases.

Figure 4:
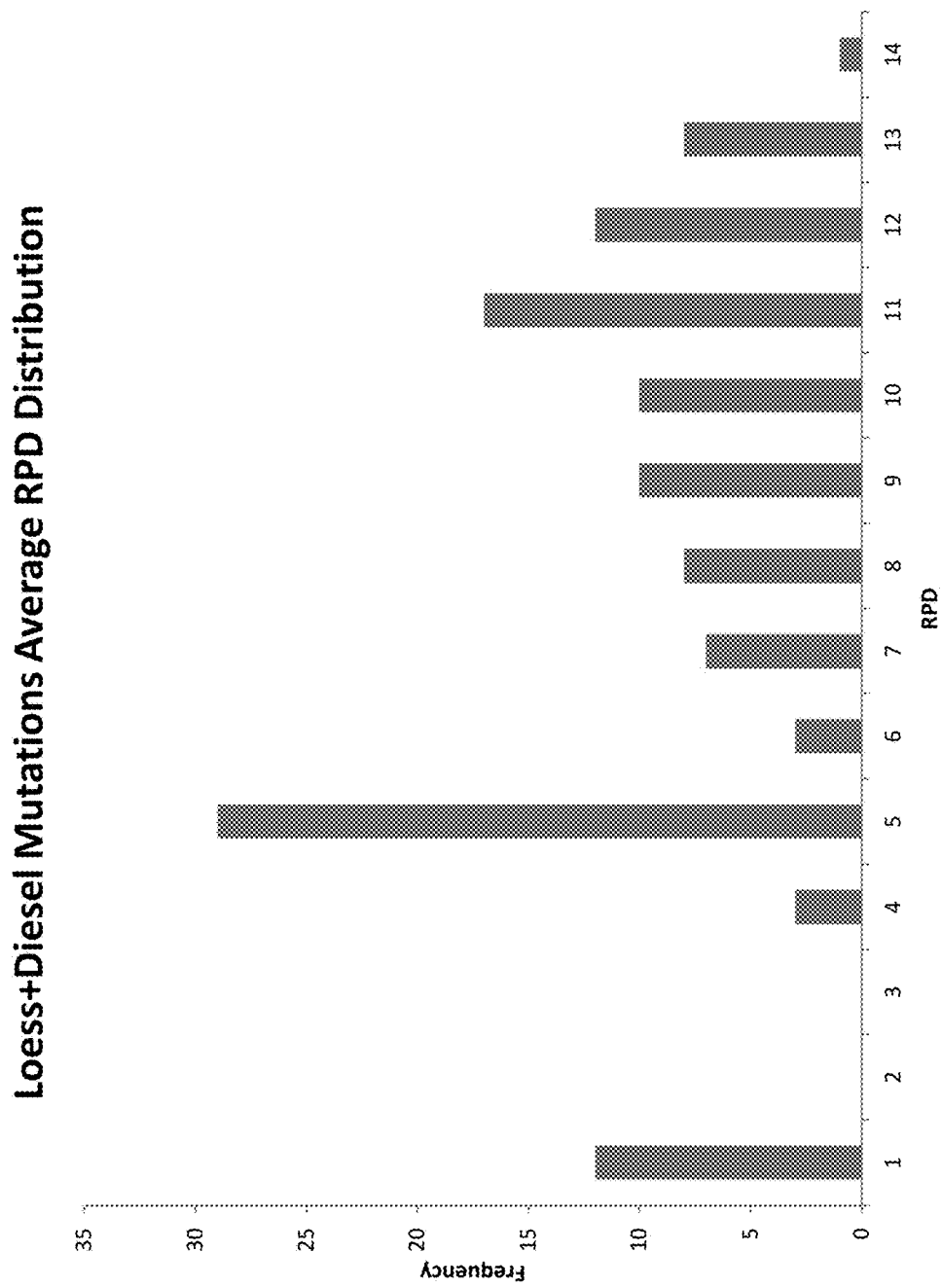
FIG. 4 is a graph showing RPD distribution for a Loess soil sample contaminated with diesel.
Figure 5:
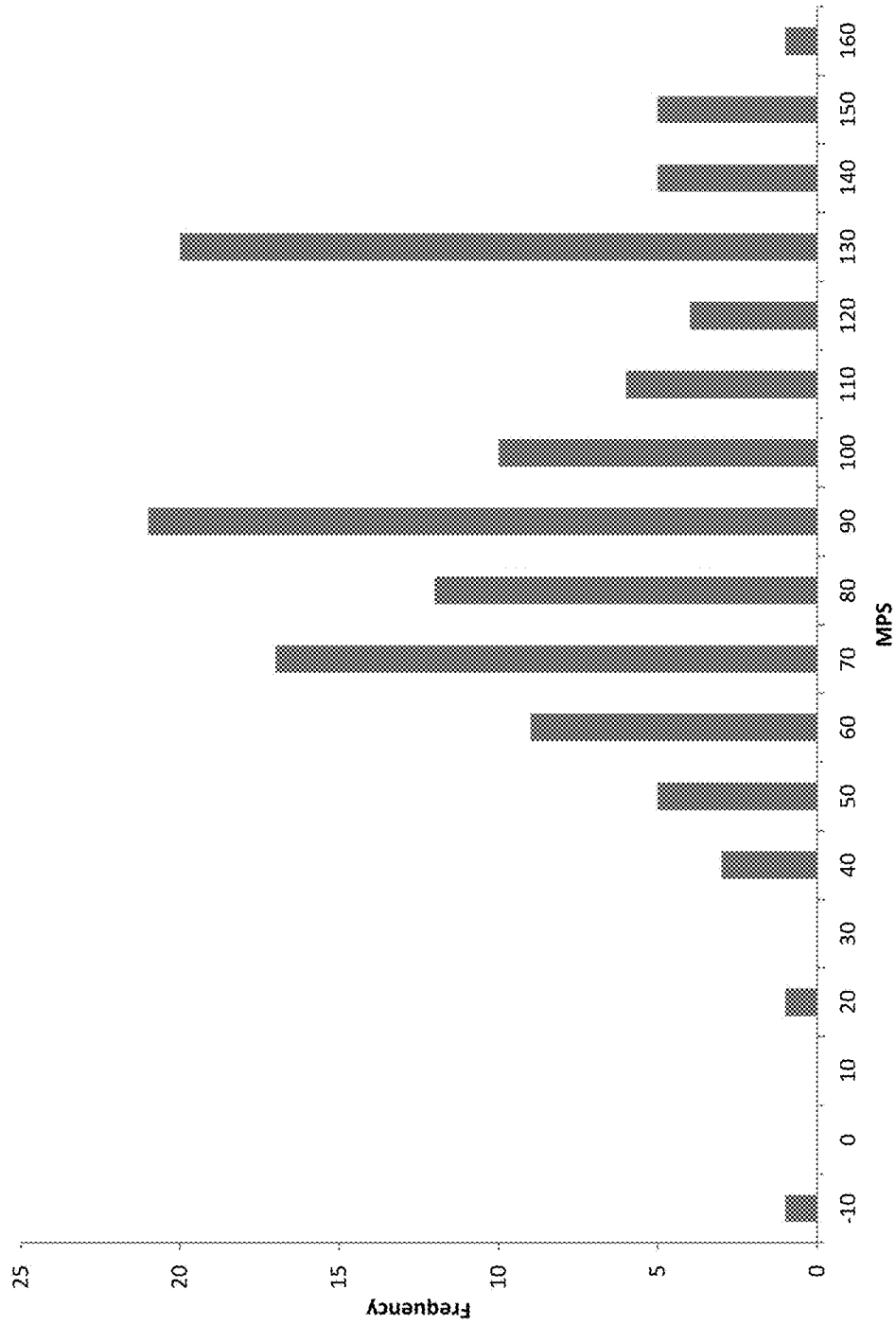
FIG. 5 is a graph showing MPS distribution for a Loess soil sample contaminated with diesel.

Reference is made in this context to the distribution of the average RPD results in FIG. 4, for the Loess+Diesel case. The score distribution of the loess contaminated with diesel dataset shows almost the same distribution, indicating the validity of the results and the importance of the preprocessing methods employed on the modeling process results. The best preprocessing method varies from dataset to dataset as shown in Table 2, indicating the relevance of using the "all possibilities" approach in the modeling process for achieving the best results.

Figure 6:
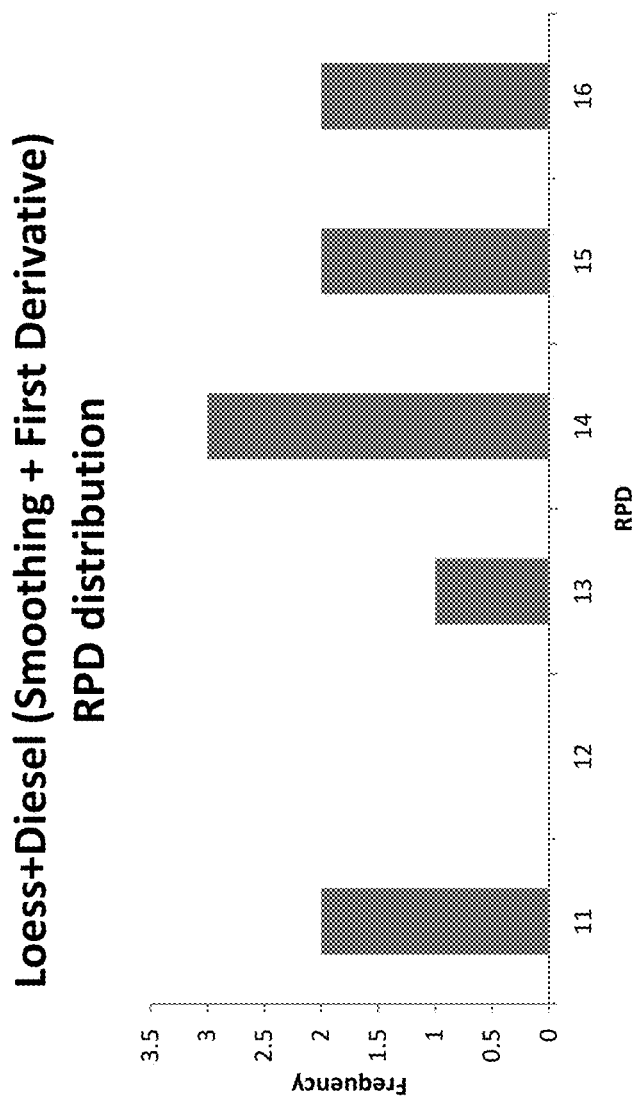
FIG. 6 is a graph showing smoothing and first derivative preprocessing for a Loess soil sample contaminated with diesel.

It is noted, that in all datasets, the best preprocessing method almost always includes some sort of normalization procedure; in a limited resource modeling situation with lack of proper modeling software or high performance computing, a normalizing preprocessing procedure may nevertheless be employed for improved performance. Due to the 10 different repetitions of the division into training/validation and test groups process that was carried out for each mutation, we may have a better understanding of the modeling process of a certain dataset. Instead of a single RPD (or any other statistical parameter) value based on a specific division, even when based on a well-known smart algorithm and not random, we now have two parameters: average RPD and RPD standard deviation. Based on these values one may better understand the modeling capabilities of the dataset and its future performances. We can see in FIG. 6 from the distribution of the RPD values for the loess contaminated with diesel dataset, that the difference between models can reach up to 50% based on the division into the training/ validation and test groups alone.

According to the present embodiments, predicting TPH levels at low concentrations in selected soils at high precision levels is viable. Modeling performance results ranged with average RPD of 4 to over 20 and MPS of 100 to over 180. We found that using the MPS parameter for model selection can yield models with equivalent performance to the best RPD selected models, but less complicated (less nLV) and more stable. Thus, we indicate the use of MPS as a new parameter for modeling performance in addition to the commonly used RPD.

Each time we divide a dataset into training, validation and test groups, although these groups represent the dataset very well, slightly different groups can be created, thus affecting the modeling process to some extent. Different preprocessing methods or their combinations need to be selected based on soil type and PHC type. Therefore, an interface for the all possibilities modeling approach was developed especially for this task. The Paracuda system enabled testing of each dataset with all 120 preprocessing mutations, as well as evaluating each modeling process 10 times for statistically quantifying the effects of the training, validation and test group selection process on the modeling performance. A review of spectroscopic and non-spectroscopic techniques for TPH and PAH determination concluded that the reflectance spectroscopy method is cheap, fast, safe, environmental friendly and has good accuracy.

In summary, reflectance spectroscopy can be used as a viable, rapid, cost effective, environmentally friendly tool to determine TPH contamination in soils. The use of the presented technology permits environmentally friendly, rapid and cost-effective measurements of many samples and therefore functions as a substitute for the costly and time consuming chemical analysis.

TABLE 2-continued

Datasets and best pretreatment mutation by RPD and MPS

| Soil | PHC | Dataset # | Best RPD Mutation | Best MPS Mutation |
|---|---|---|---|---|
| Rendzina | 95 | 10 | SAfD | SfDCr |
| | Diesel | 11 | Cr | SNVfDfS |
| | Kerosene | 12 | SfDCr | SfDCr |
| Terra Rosa | 95 | 13 | MSC | SAfD |
| | Diesel | 14 | AfD | AfD |
| | Kerosene | 15 | sDCr | sD |

It is expected that during the life of a patent maturing from this application many relevant pulse shaping and symbol decoding technologies will be developed and the scope of the corresponding terms in the present description are intended to include all such new technologies a priori.

The terms "comprises", "comprising", "includes", "including", "having" and their conjugates mean "including but not limited to".

The term "consisting of" means "including and limited to". As used herein, the singular form "a", "an" and "the" include plural references unless the context clearly dictates otherwise.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as

TABLE 1

Soil Properties

| Israeli Classification | USDA Classification | HM % | Sand | Silt volume % | Clay | SOC | SIC g kg$^{-1}$ | Total N | pH$^1$ | EC$^1$ mS m$^{-1}$ | SSA m$^2$ g$^{-1}$ |
|---|---|---|---|---|---|---|---|---|---|---|---|
| Loess | Tipic Xerofluvent | 4.14 | 38.6 | 49.4 | 12 | 5.4 | 22.5 | 0.9 | 8.22 | 5.44 | 167 |
| Hamra | Tipic Xerocherept | 1.44 | 97.37 | 1.73 | 0.9 | 1.5 | 2.1 | 0.5 | 8.57 | 0.08 | 83 |
| Gromosol | Typic Chromoxerert | 5.23 | 46.46 | 38.98 | 14.56 | 7.6 | 12.5 | 1.3 | 8.68 | 0.55 | 238 |
| Terra Rosa | Lithic ruptic Xerochrept | 9.14 | 19.89 | 57.14 | 22.97 | 20.9 | 15.5 | 2.6 | 7.71 | 0.36 | 380 |
| Rendzina | Lithic Haploxeroll | 5.63 | 2.19 | 77.61 | 20.2 | 11.5 | 70.5 | 1.7 | 7.79 | 0.45 | 262 |

TABLE 2

Datasets and best pretreatment mutation by RPD and MPS

| Soil | PHC | Dataset # | Best RPD Mutation | Best MPS Mutation |
|---|---|---|---|---|
| Gromosol | 95 | 1 | fDCrfS | sD |
| | Diesel | 2 | Cr | SfDCrfS |
| | Kerosene | 3 | Cr | fDCr |
| Hamra | 95 | 4 | AfD | AsDCr |
| | Diesel | 5 | SfDCrfS | SSNVfDfS |
| | Kerosene | 6 | Cr | SSNVfDfS |
| Loess | 95 | 7 | fDCr | fDCr |
| | Diesel | 8 | SfD | SfD |
| | Kerosene | 9 | S | SSNVfS | prior art to the present invention. To the extent that section headings are used, they should not be construed as necessarily limiting.

What is claimed is:

1. Method for quantitative assessment of chemical constituents of a substance using reflectance spectroscopy, the method comprising:
   obtaining a plurality of samples of said substance, the samples having respective chemical constituents;
   spectrally analyzing each sample of said substance using reflectance spectroscopy, said reflectance spectroscopy obtaining spectroscopy data of said respective sample;
   applying to said sample spectroscopy data of each respective sample of said substance a plurality of combinations from a set of preprocessing operations;
   removing ones of said combinations;
   from each remaining combination generating a respectively different version of said sample spectroscopy data, each version being a respective perturbation of the sample spectroscopy data, each perturbation thereby being generated according to a respective one of said combinations of preprocessing operations, wherein said set of preprocessing operations comprises initial smoothing, multiplicative scatter correction, signal normal variate, absorption, continuum removal, first derivative, second derivative, and final smoothing;
   using all of said perturbations, generating a model relating said preprocessed spectral data to respective chemical constituents, and
   using said model with spectroscopy data of an additional sample of said substance having unknown chemical constituents to determine respective unknown chemical constituents thereby characterizing the chemical constituents of said additional sample of said substance.

2. The method of claim 1, wherein said building a model comprises:
   using said respectively different data sets, extracting latent variables;
   retrieving a first latent variable and making a first prediction of said different chemical constituents;
   adding a candidate second latent variable and making a second prediction of said different chemical constituents, and if said second prediction is more accurate than said first prediction then retaining said candidate second latent variable but if said second prediction is not more accurate than said first prediction then discarding said candidate second latent variable and repeating with a different candidate second variable;
   iteratively adding further candidate latent variables, and repeating said prediction of said different chemical constituents, in each case retaining respective candidate latent variables if a corresponding prediction of said different chemical constituents is more accurate than a preceding estimate;
   continuing said process until reaching a predetermined number of latent variables.

3. The method of claim 2, further comprising verifying said model, prior to said using, by further predicting of chemical constituents of a verification set of additional samples with known chemical constituents.

4. The method of claim 1, wherein said spectroscopy comprises visible or near infra-red spectroscopy.

5. The method of claim 4, wherein said spectrally analyzing is carried out within a wavelength range lying between 350 and 2500 nm.

6. The method of claim 1, wherein said set of different preprocessing operations comprises data mining operations, said data mining operations in turn comprising both linear and non-linear algorithms.

7. The method of claim 6, wherein said set of different data mining operations comprises at least two members of the group consisting of: artificial neural networks, genetic algorithms, support vector machines, fuzzy logic, partial least squares, multiple linear regression, metric learning and principle component regression.

8. The method of claim 1, comprising using between a third and a half of all possible combinations of said preprocessing operations.

9. The method of claim 1, comprising using all possible combinations of said preprocessing operations of said set except for combinations that, contain mutually incompatible preprocessing operations and combinations that provide results that, are complex numbers.

10. The method of claim 1, wherein said building said model further comprises using a model performance scoring parameter (MPS) defined as:

$$MPS = \%stability + NRPD - NRMSEP - NnLV$$

wherein said % Stability is obtained by dividing a number of stable models by a number of repetitions for each respectively different data set, said NRPD is a normalized average of a ratio of prediction to deviation, said NRMSEP is a normalized root mean square error in prediction, and said NnLV is a normalized predetermined optimal number of latent variables.

11. The method of claim 1, further comprising arranging said pre-processed spectroscopy data into datasets using conditioned Latin Hypercube Sampling.

12. The method of claim 1, comprising taking said plurality of different samples from a plurality of different chemical constituent types.

13. A testing device for testing samples of a substance for chemical constituents, the testing device comprising:
   a current test sample of said substance, the current test sample having one or more unknown chemical constituents;
   a spectrometer or spectral imager configured to carry out reflectance spectroscopy on said current test sample, thereby to obtain a spectral data set from said current test sample;
   a spectral preprocessor configured to carry out a plurality of different combinations of a set of predefined preprocessing operations, each combination providing a different perturbation of said spectral data set, said spectral preprocessor further configured to remove ones of said combinations;
   a parameterizer, configured to obtain current sample spectral parameters from remaining ones of said combinations, thereby obtaining parameters of respectively different perturbations of said data set, each perturbation thereby being generated according to a respective one of said combinations of preprocessing operations, wherein said set of preprocessing operations comprises initial smoothing, multiplicative scatter correction, signal normal variate, absorption, continuum removal, first derivative, second derivative, and final smoothing:
   a model relating sets of spectral parameters obtained from spectroscopy data to respective associated one or more chemical constituents; and
   a spectral comparator configured to compare spectral parameter sets of said model with said spectral parameters of said current sample of said substance to find a set from said model that matches said spectral parameters of said current sample of said substance, said model thereby identifying a respective associated one or more chemical constituents; and an output for indicating said respective associated one or more chemical constituents, thereby characterizing said current test sample in terms of its chemical constituents.

\* \* \* \* \*